United States Patent [19]
Sheffield

[11] Patent Number: 5,428,407
[45] Date of Patent: Jun. 27, 1995

[54] PRESCRIPTION LENS ATTACHABLE TO SAFETY GLASSES

[76] Inventor: Keith W. Sheffield, Park Cottage, TN12 7NQ, Brenchley, Kent, England

[21] Appl. No.: 167,105

[22] Filed: Dec. 15, 1993

[51] Int. Cl.6 .......................... G02C 7/08; G02C 9/04
[52] U.S. Cl. ......................................... 351/58; 351/41; 351/57; 351/158; 2/441; 2/445
[58] Field of Search ........................ 351/41, 44, 58, 63, 351/158, 47, 52, 57, 59, 86, 130, 133, 140, 154, 155; 2/442, 443, 444, 445, 446, 431, 441, 13

[56] References Cited

U.S. PATENT DOCUMENTS

| | | | |
|---|---|---|---|
| 3,628,854 | 12/1971 | Jampolsky | 351/175 |
| 3,787,113 | 1/1974 | Shedrow | 351/158 X |
| 4,247,178 | 1/1981 | Cook | 351/47 |
| 4,563,065 | 1/1986 | Kreissl | 351/86 |
| 4,717,249 | 1/1988 | Fischer | 351/43 |
| 4,810,080 | 3/1989 | Grendol et al. | 351/158 X |
| 5,026,150 | 6/1991 | Weber | 351/57 X |
| 5,153,619 | 10/1992 | Nix | 351/57 |

FOREIGN PATENT DOCUMENTS

| | | | |
|---|---|---|---|
| 1489383 | 7/1967 | France. | |
| 2923798 | 12/1979 | Germany | 351/41 |

OTHER PUBLICATIONS

Set#1-6 color photographs of main frame no date.
Set#2-3 color photographs of frame no date.
Set#3-2 color photographs of frame no date.
"Introducing RACAL Intego, The complete integrated safety system" brochure–no date.
2 pages, from Bolle' America, Inc./Sport Optical System no date.

Primary Examiner—William L. Sikes
Assistant Examiner—David R. Parsons

[57] ABSTRACT

A prescription lens attachable to a safety glass frame. The safety glass frame is provided with a single lens, a center cross pin and indentation on an inner surface of the safety glass frame juxtaposed the temple pivot pin. A prescription frame includes separate prescription lenses and a central clip that clips onto the cross pin of the safety glass frame. The outer ends of the prescription frame are provided with angular locking ends that are pressed into the indentation on the safety glass frame. Thus, the prescription lens frame is held securely onto the safety glass frame between the safety glass frame and the persons eyes. Damage to the safety glass lens or frame necessitate replacement of only the non-prescription safety glasses because the prescription frame can be removed from the damaged frame and secured to a new safety glass frame.

3 Claims, 2 Drawing Sheets

PRESCRIPTION LENS ATTACHABLE TO SAFETY GLASSES

BACKGROUND OF THE INVENTION

This invention is directed to a lens for use with safety glasses and more particularly to a prescription lens for safety glasses which is snapped onto the inside surfaces of the frame for safety glasses. Thus, the safety glasses can be made plain without a prescription wherein the prescription safety glass lenses are made for a specific person and secured onto the inside of the glass frame.

Heretofore supplemental lenses have been used for various types of glass frames which include regular glass and masks. Such known glasses include an adhesive bifocal lens U.S. Pat. No. 5,153,619. A thin plastic membrane which is applied to a spectacle U.S. Pat. No. 3,628,854. German patent 2,923,798 is directed to swim goggles to which corrective lenses have been bonded. U.S. Pat. No. 4,717,249 illustrates a prism lens applied to a mask for improved vision. U.S. Pat. No. 4,563,065 shows a multiple lens from which separate lenses can be torn off for use in a mask. The lens has means for securing the lens in a mask. French patent 1,489,383 sets forth a foldable lens which is attached to the temple of a frame. Other lenses are available and can be used with glasses or masks.

Two pair of prior art glasses have become known which are of interest. One pair of glasses makes use of a frame which has an outward projecting rim along the inner surface of the lens which forms a recess substantially around the frames excepting in a center upper portion. The insert has a sloping edge which snaps under the projecting rim in order to hold the insert on the inside of the frame. The insert fits under the projecting rim and is held in place by a snap fit. The other pair of glasses has a projecting rim entirely around the inside of the frame surrounding the main lens. The frame has a center top projection with a central protrusion under which a U-shaped portion of the rim of the insert fits. The remaining portion of the insert has a sloping rim surface which snaps into the projecting rim of the frame so that the insert snaps under the projecting rim and under the projecting upper center piece.

OBJECT AND SUMMARY OF THE INVENTION

It is therefore an object of the invention to provide a prescription lens for a specific person in which the lens is secured to an inside of a frame including safety glasses.

Lenses made in accordance with this invention include a frame with corrective prescription lenses in the frame in which the frame is secured to the inside of the frame of safety glass glasses without disturbing the viewing area of the person. Such prescription lenses can be made for a particular person and then added to a pair of regular safety glasses without a requirement for any prescription glass lenses within the safety glasses. In carrying out this invention, all safety glasses can be made with non-prescription glass lenses to be worn by any person and then the prescription glasses can be made with regular prescription lenses without a requirement that the prescription glasses be made of safety glass. In this type of combination glasses, the safety glasses can be made without prescription lenses wherein the prescription lenses for a particular person is made and secured within the confines of the safety glass between the safety glass and the eyes. Therefore, if the safety glasses are broken or damaged, replacement of the safety glass will be much less expensive and more quickly because the safety glass lenses are not of a particular prescription.

DETAILED DESCRIPTION OF THE PREFERRED EMBODIMENT

Figure 1:
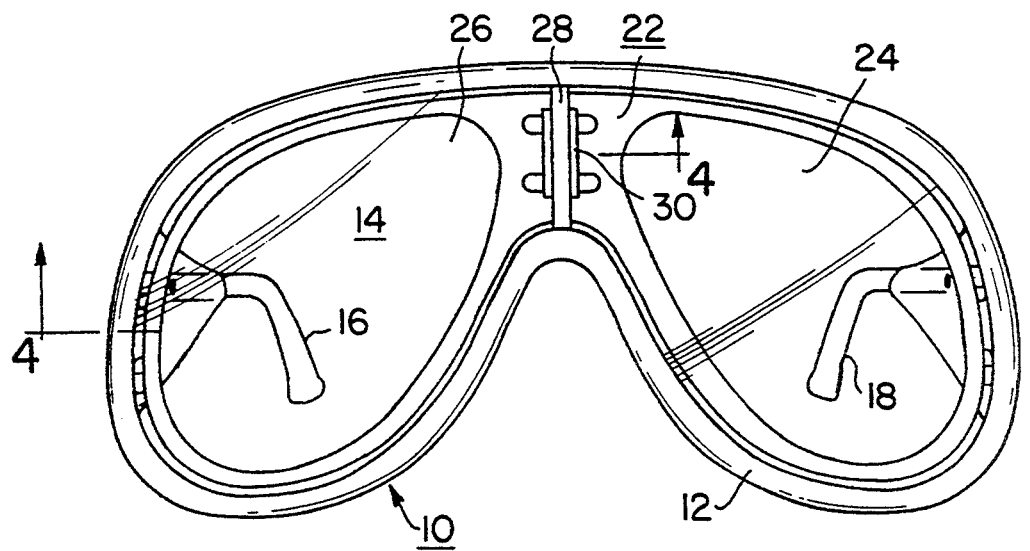
FIG. 1 illustrates a front view of a pair of safety glasses in which prescription lenses have been secured.
Figure 2:
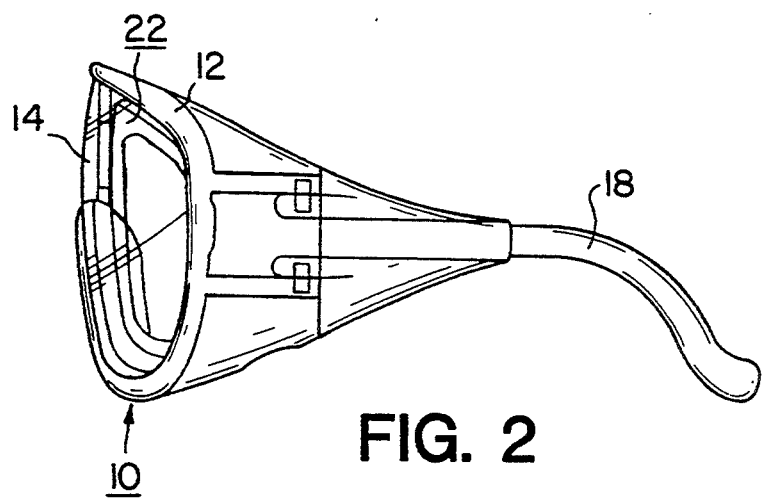
FIG. 2 illustrates a side view of the safety glasses with the prescription lenses secured with the safety glass frame.
Figure 3:
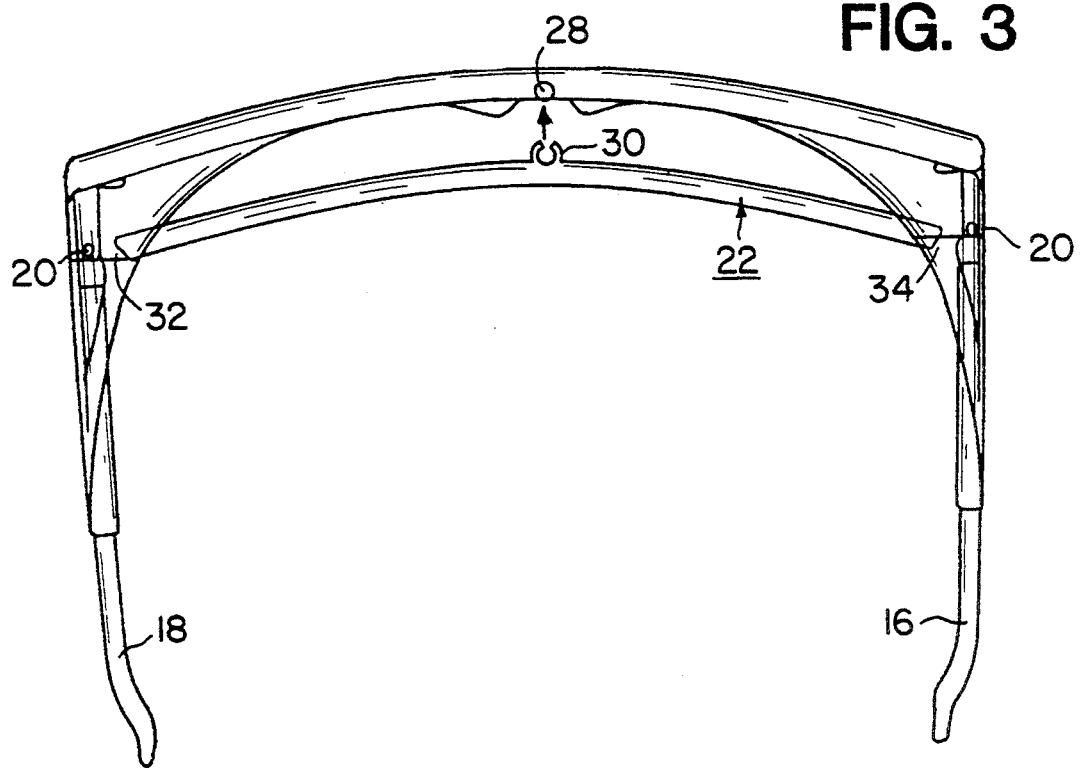
FIG. 3 illustrates a top view of a pair of safety glasses with the prescription lens insert spaced from the safety glass frame ready to be secured to the safety glass frame.
Figure 4:
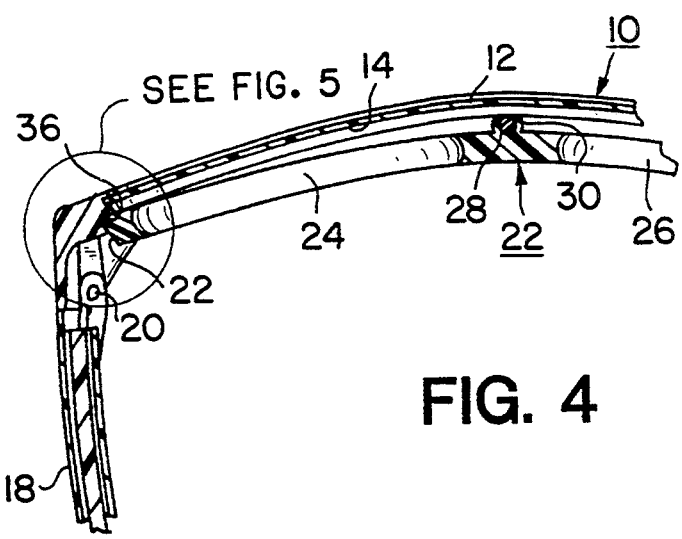
FIG. 4 is a cross sectional view illustrating the prescription lens attached to the safety glass frame.
Figure 5:
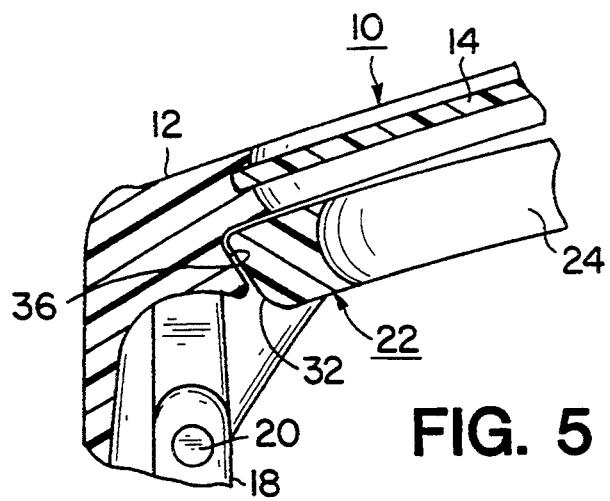
FIG. 5 is an enlarged view shown in the circled area shown of FIG. 4.

Now referring to the drawings wherein the same elements are noted by the same reference characters throughout the drawings, there is shown in FIGS. 1–5 a pair of safety glasses 10 having a frame 12 a single non-prescription lens made of safety glass 14 secured within the safety glass frame which is made of plastic and temples 16, 18 secured to opposite sides of the safety glass frame for pivoting on pivot pins 20. A prescription glass frame 22 also made of plastic includes separate prescription lenses 24, 26 therein in which the frame 22 is secured to or for securing to the safety glasses frame 12. The safety glass frame 12 includes a cylindrical center cross pin 28 that extends across the one piece lens from the top of the frame to the bottom of the frame. The prescription glass frame is provided with a somewhat U-shaped clip 30. Said somewhat U-shaped clip is formed by linear oppositely disposed arcuate ends that face each other and are constructed from a resilient material. The arcuate ends face the cross pin 28 on the safety glass frame and which clips onto the cross pin 28. The prescription glass frame is also provided with angle shaped outer ends 32 and 34 each of which are pressed into angular indentations, only one of which 36 is clearly shown in the drawings on the inner surface of the safety glass frame in the vicinity of the end of the temples.

The clip 30 is provided with an inner diameter which is substantially the same as the diameter of the cross pin 28. The ends of the clip toward the pin 28 are somewhat spring loaded and forced outwardly as the clip is forced onto the pin 28 so that the outer ends of the clip will spring back around the pin 28 in order to hold the center of the prescription frame to the safety glass frame. The outer ends of the prescription frame are pressed into the angled indentations of the safety glass frame so that the outer ends of the prescription frame will be held in place by the safety glass frame.

It is obvious to one skilled in the art that a pair of safety glasses can be made with a single non prescription lens or separate lens for as many employees as desired with some in storage. In case one of the safety glass lens or frame is broken it can be readily replaced. The prescription lenses are made for specific personnel and set in a prescription frame for use by the particular person. Thus, if the safety glasses are damaged or broken, all the user has to do is remove the prescription lens frame from the broken safety glass frame and replace the prescription frame into the safety glass frame.

It is well known that in certain areas of work that all personnel in the area should wear safety glasses. Only those that require prescription glasses will be required to add the prescription glasses to the safety glass frame. Glasses such as set forth herein will permit making the safety glasses with a single lens which will be cheaper than making two separate lenses. Also, all safety glasses can be made alike which will cost less on a mass production basis. The lenses of the prescription glass insert need not be safety glass; therefore, the prescription lenses can be made at a lesser cost. Further replacement of a broken or damaged safety glass will cost less since the person can use the same prescription lens inserted into a new safety glass frame.

The foregoing relates to a preferred exemplary embodiment of the invention, it being understood that other variants and embodiments thereof are possible within the spirit and scope of the invention, the latter being defined by the appended claims.

What is claimed and desired to be secured by Letters Patent of the United States is:

1. A pair of safety glasses in combination with a pair of separate prescription glasses, said prescription glasses adapted to be secured on an inside of said pair of safety glass in which said safety glasses include a safety glass frame, at least one lens in said safety glass frame, a central vertical cross pin which extends from an upper frame portion to a lower frame portion at a bridge area, and a pair of pivotable temples secured to said safety glass frame by a pair of pivot pins said safety glass frame including oppositely disposed angular indentations in said safety glass frame which angle inwardly juxtaposed said pivot pins, said prescription glasses including a frame, a pair of prescription lenses in said frame, a central clip in an area of a bridge which clips onto said central vertical cross pin of said safety glass frame, in a direction toward said safety glass frame vertical cross pin, and said prescription glasses include end portions which mate with and seat in said indentations of said safety glasses to secure said prescription glasses onto said safety glasses by use of only three connecting parts.

2. The claim as set forth in claim 1, wherein said vertical cross pin is cylindrical and said central clip includes oppositely disposed linear arcuate ends that conform to the cylindrical shape of said vertical cross pin to fit onto said vertical cross pin and said prescription glasses are secured to said safety glasses only by use of said central clip and said end portions.

3. The claim as set forth in claim 2 in which said end portions of said prescription glasses have angled ends in an area of said pivot pins which interfit only with said angular indentations in said safety glass frame juxtaposed said pivot pins in order to assist in securing said prescription lens frame within said safety glass frame.

* * * * *

UNITED STATES PATENT AND TRADEMARK OFFICE
CERTIFICATE OF CORRECTION

PATENT NO. : 5,428,407
DATED : June 27, 1995
INVENTOR(S) : Keith W. Sheffield It is certified that error appears in the above-identified patent and that said Letters Patent is hereby corrected as shown below:

On the title page: Item

[73] Crews, Inc., Memphis, Tennessee

Signed and Sealed this

Seventh Day of November, 2000

Attest:

Q. TODD DICKINSON

*Attesting Officer*      *Director of Patents and Trademarks*